(12) United States Patent
Suzuki et al.

(10) Patent No.: US 6,215,549 B1
(45) Date of Patent: Apr. 10, 2001

(54) APPARATUS FOR MEASURING OPTICAL CHARACTERISTICS

(75) Inventors: Takashi Suzuki, Yokohama; Yoshinori Ohsaki, Utsunomiya, both of (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/204,270

(22) Filed: Dec. 3, 1998

(30) Foreign Application Priority Data

Dec. 8, 1997 (JP) .................................................. 9-337537

(51) Int. Cl.⁷ .................................................. G01N 21/49
(52) U.S. Cl. ........................ 356/33.8; 356/445; 356/369
(58) Field of Search .................................. 356/445, 446, 356/336, 337, 338, 364, 368, 369

(56) References Cited

U.S. PATENT DOCUMENTS

| | | | |
|---|---|---|---|
| 3,975,084 | * | 8/1976 | Block ..................................... 356/359 |
| 5,017,009 | * | 5/1991 | Schutt et al. .......................... 358/338 |
| 5,666,197 | * | 9/1997 | Guerra ................................. 356/335 |
| 6,088,115 | * | 7/2000 | Ohsaki et al. ........................ 356/445 |

FOREIGN PATENT DOCUMENTS

| | | |
|---|---|---|
| 6-82239 | 3/1994 | (JP) . |
| 9-105704 | 4/1997 | (JP) . |
| 10-68673 | 3/1998 | (JP) . |

OTHER PUBLICATIONS

J. Xue, et al., "Surface Orientation Transitions in Surface Stabilized Ferroelectric Liquid Crystal Structures," *Applied Physics Letters*, vol. 53, No. 24, Dec. 12, 1988, pp. 2397–2399.

"Determination of Liquid–Crystal Pretilt Angle in a Small Area with a Size of Micron Meters", Yoshinori Ohsaki, et al., Technical Digest, the Fifth Microoptics Conference (MOC '95 Hiroshima), G10, 1995, pp. 144–147.

* cited by examiner

Primary Examiner—Richard A. Rosenberger
(74) Attorney, Agent, or Firm—Fitzpatrick, Cella, Harper & Scinto

(57) ABSTRACT

An optical characteristic measuring apparatus capable of making a measurement area smaller and facilitating the precise checking of the position of the measurement area includes a filter having a small hole disposed between a semispherical glass and a photodetector, so that a light beam reflected at a specific interface is detected with the photodetector and a light beam reflected at an interface different from the specific interface is not detected with the photodetector. By this arrangement, measurement precision by the photodetector can be maintained. Moreover, since a conventional upper semispherical glass is not placed on a liquid crystal device, the position of a measurement area can be precisely checked easily with a microscope.

19 Claims, 7 Drawing Sheets

APPARATUS FOR MEASURING OPTICAL CHARACTERISTICS

BACKGROUND OF THE INVENTION

1. Field of the Invention

The present invention relates generally to an apparatus of measuring the optical characteristics of the boundary area of a given medium to be inspected.

2. Related Background Art

The following conventional methods are known, which measure various optical characteristics by using total internal reflection of light.

(1) TIR Method (a total internal reflection method, J. Z, Xue, N. A. Clark, and M. R. Meadows, Appl. Phys. Lett. 53, p. 2397 (1988)).

(2) Calibration Curve Method (JP-A-6-82239)

As an example of an optical-characteristic measuring apparatus that utilizes each of the above methods, an optical anisotropy measuring apparatus for measuring a pre-tilt angle of liquid crystal will be described.

(1)-1 Optical anisotropy measuring apparatus utilizing the TIR method (Prior Art 1)

FIG. 1 is a schematic diagram showing an example of the structure of an optical anisotropy measuring apparatus utilizing the TIR method and illustrating an optical anisotropy measuring method. This optical anisotropy measuring apparatus 1 has a glass member of a semispherical shape (hereinafter called a "semispherical glass"). As shown in detail in FIG. 2, this semispherical glass 2 has a flat part 2a and a spherical part 2b. A glass substrate 3 is disposed facing the flat part 2a. On the surfaces of the glass substrate 3 and flat part 2a, transparent electrodes 5 and orientation films 6 are formed. The glass substrate 3 and flat part 2a are bonded together by a sealing member 7. Liquid crystal 9 as a medium to be inspected is filled in a space between the glass substrate 3 and flat part 2a.

The semispherical glass 2 is supported by an unrepresented rotation mechanism to rotate the spherical glass 2 about a rotary axis C normal to the flat part 2a. The refractive index of the semispherical glass 2 is set larger than that of the polarization film 6 and liquid crystals 9. The film thickness of the orientation film 6 is made smaller than the wavelength of an applied light beam A1 (the details will be given later).

An He—Ne laser source 10 is disposed on one side (lower left in FIG. 1) of the semispherical glass 2 and applies the light beam A1 to the semispherical glass 2 along a downward oblique direction relative to the flat part 2a (the light beam A1 applied to the liquid crystal 9 from the He—Ne laser source 10 is called hereinafter an "incidence light beam A1"). A photodetector 11 is disposed on the other side (lower right in FIG. 1) of the semispherical glass 2 and detects a light beam B1 totally reflected from the interface to the liquid crystal 9 (the light beam B1 totally reflected is hereinafter called a "reflection light beam B1").

A polarizer 12 is disposed between the semispherical glass 2 and He-Ne laser source 10 and linearly polarizes the incidence light beam A1 from the He-Ne laser source 10. An analyzer 13 is disposed between the semispherical glass 2 and photodetector 11 and has a polarization direction perpendicular to the polarizer 12.

Next, an optical anisotropy measuring method (a pre-tilt angle measuring method) using the above-described optical anisotropy measuring apparatus will be described.

The incidence light beam A1 output from the He—Ne laser source 10 is linearly polarized by the polarizer 12 into p-polarization relative to the incidence plane of total internal reflection, and applied to the semispherical glass 2. This incidence light beam A1 is totally reflected by an interface between the transparent electrode 5 and orientation film 6. Evanescent light, generated when the total reflection occurs, enters once the liquid crystal and then is reflected. This evanescent light changes its polarization state in accordance with the optical anisotropy of liquid crystal near at the interface to the orientation film 6.

Of the reflection light beam B1 output from the semispherical glass 2, only the components (s-polarization components) having a polarization direction perpendicular to the polarizer 12 pass through the analyzer 11.

As the semispherical glass 2 together with the glass substrate 3 and the like is rotated about the rotary axis C, the direction of a director, which is a unit vector representative of the direction of a liquid crystal molecule of the liquid crystal 9, changes with the direction of an electric field of the incidence light beam A1. Therefore, the polarization state of the reflection light beam B1 output from the semispherical glass 2 changes with the rotational angle of the semispherical glass 2. By plotting an output of the photodetector 11 relative to the rotational angle of the semispherical glass 2, a characteristic curve representative of the optical anisotropy of the liquid crystal, such as shown in FIG. 3, can be obtained. The pre-tilt angle can be calculated from a ratio of Imax/Imin, where Imax is a maximum extreme intensity and Imin is a minimum extreme intensity. The larger the pre-tilt angle, the smaller the ratio of Imax/Imin becomes, whereas the smaller the pre-tilt angle, the larger the ratio of Imax/Imin becomes.

With the optical anisotropy measuring apparatus 1 described above, the optical anisotropy or pre-tilt angle of the liquid crystal 9 is calculated in accordance with a change in the polarization state of the reflection light beam B1 to be caused by the interaction between the liquid crystal molecules and the evanescent light generated when the total reflection occurs.

The measurement area (an ellipsoid having a minor axis of about 0.6 mm and a major axis of about 3 mm) of the optical anisotropy measuring apparatus 1 is larger than the size (a square of 30 to 50 $\mu$m) of one pixel of a liquid crystal device used with a display or the like. Therefore, the orientation state of each unit pixel cannot be measured so that the orientation states of pixels cannot be compared. It is also difficult to detect a variation in orientation directions of one pixel. It is also impossible to detect a fine defect smaller than, for example, 8 $\mu$m and it is difficult to compare the orientation state of a defect area with that of another area. From the above reasons, the orientation state of the liquid crystal 9 cannot be detected correctly and it is difficult to elucidate the mechanism of defect formation.

(1)-2 Optical anisotropy measuring apparatus utilizing the TIR method (Prior Art 2).

To solve the above problems, an apparatus 20 shown in FIG. 4 has been proposed (JP-A-9-105704) which has an input side optical system 31 disposed between an He—Ne laser source 10 and a semispherical glass 2 to converge an incidence light beam A1 and make the measurement area small (a major axis of about 10 to 30 $\mu$m). In FIG. 4, reference numeral 22 represents a liquid crystal device, and reference symbol A2 represents an incidence light beam converged by the input side optical system 31. The major axis of the measurement area of this apparatus 20 is about 8 $\mu$m.

(1)-3 An optical anisotropy measuring apparatus utilizing the TIR method (Prior Art 3).

In the Prior Art 1, the orientation film 6 is formed directly on the side of the semispherical glass 2. However, it is very difficult to form good medium samples by subjecting the orientation film 6 to a rubbing process.

To form a good medium, an apparatus has been proposed (JP-A-9-105704) that uses a discrete liquid crystal device and a discrete semispherical glass 2. With this apparatus, since the liquid crystal device is movable relative to the semispherical glass 2, a variation of pre-tilt angles can be measured (refer to Technical Digest, the Fifth Microoptics Conference (MOC' 95 Hiroshima), G10, p. 144, by Y. Ohsaki and T. Suzuki).

(1)-4 An optical anisotropy measuring apparatus utilizing the TIR method (Prior Art 4).

The major axis of the measurement area of Prior Art 2 is about 8 μm. An optical anisotropy measuring apparatus 30, such as shown in FIG. 5, has been proposed (in JP-A-9-148283) which makes the major axis smaller.

This optical anisotropy measuring apparatus 30 has two upper and lower semispherical glasses 2 (hereinafter called an "upper semispherical glass 2" and a "lower semispherical glass 2" when discrimination therebetween is necessary). Each of the semispherical glasses 2 has a flat part 2a and a spherical part 2b. The semispherical glasses 2 are disposed facing each other at a predetermined distance between the flat parts 2a and 2a.

A liquid crystal device 22 is disposed between the semispherical glasses 2. As detailed in FIG. 6, the liquid crystal device 22 has a pair of glass substrates, and a transparent electrode 5 and an orientation film 6 are formed on the surface of each of the glass substrate 23. The glass substrates 23 are bonded together by a sealing member 7. Liquid crystal 9, as a medium to be inspected, is filled in between the orientation films 6.

Refractive index matching liquid 25 is filled in between the liquid crystal device 22 and each semispherical glass 2, the liquid having generally the same refractive index as the glass substrate 23 and semispherical glass 2. Therefore, reflection does not occur at the interface between the liquid crystal device 22 and each semispherical glass.

An input-side optical system 31 is disposed between a polarizer 12 and the lower semispherical glass 2. An He—Ne laser source 10, a polarizer 12, and an input side optical system 31 are disposed so that a partial light beam A3 becomes incident at an angle smaller than a critical angle θc. A fraction of the light beam B3 transmits through liquid crystal 9, the light beam transmitting through the liquid crystal 9 being called a "transmission light beam B3".

On the opposite side of the lower semispherical glass 2, an output side optical system (second optical system) 32, an analyzer 13, and a photodetector 11 are disposed so that a reflection light beam B2, totally reflected at the liquid crystal interface, is detected with the photodetector 11, which measures optical anisotropy to detect the orientation state of the liquid crystal interface.

Also with this apparatus 30, the pre-tilt angle can be calculated by the method that is the same as in Prior Art 1.

In this case, however, the light beam to be measured is the light beam B2 incident upon the liquid crystal at an angle larger than the critical angle θc and totally reflected at the liquid crystal interface. The partial light beam A3 is incident upon the liquid crystal at an angle smaller than the critical angle θc so that it is not totally reflected, but most of the partial light beam is transmitted through the liquid crystal 9 and becomes the transmission light beam B3, and the remaining light beam becomes an ordinary reflection light beam. This ordinary reflection light beam has an unchanged polarization state different from the totally reflected evanescent light, and cannot transmit through the analyzer and cannot be detected with the photodetector 11. The spherical area 2b of the upper semispherical glass 2 disposed on the liquid crystal device 22, with refractive index liquid 25 being interposed therebetween, is formed with an antireflection film. Therefore, the transmission light beam B3 is neither reflected at the interface to the antireflection film nor detected with the photodetector 11.

With this apparatus 30, since the partial light beam A3 is made incident at an angle smaller than the critical angle θc, the numerical aperture NA becomes large and the light beam A2 incident upon the liquid crystal 9 is more strongly converged (specifically being able to be converged to a light flux diameter of 2 μm or smaller) so that the measurement area can be made about 5 μmφ or less. Therefore, the light beam illumination area on the liquid crystal interface becomes circular from a conventional ellipsoidal shape.

Under such coherent illumination, the diameter (measurement area) of a focal point is given by:

$$1.4\lambda \sqrt{(N^{2+0.25/n})}$$

where N is a f-number of a lens of the input side optical system 31, λ is a wavelength of the incidence light beam A2, and n is the refractive index of the glass substrate 23. If the refractive index of the liquid crystal 9 is 1.5 and the refractive index of the semispherical glass 2 and glass substrate 23 is 1.8, then the total reflection critical angle Oc is represented by sin θc=1.5/1.8, i.e., the critical angle θc is 56.4°. If λ=0.63 μm and the incidence angle θ=45°, the diameter (measurement area) of a focal point is about 0.8 μm at N=1 and about 1.1 μm at N=1.5.

Since the measurement area is made considerably small as compared to the size of one pixel of the liquid crystal, the distribution of pre-tilt angles in one pixel can be measured and the orientation states of the liquid crystal 9 in a fine defect area and in a nearby area can be measured. Therefore, this apparatus 30 is a very effective means not only for the development of the liquid crystal 9 and orientation film but for the development of orientating methods themselves.

(2)-1 An optical anisotropy measuring apparatus utilizing the calibration curve method (Prior Art 5).

This apparatus has a similar structure to that of the apparatus of Prior Art 1 (FIG. 1) because total reflection is utilized. However, a different point is that it is not necessary to rotate a semispherical glass 2. An analyzer 13 is also unnecessary. Incidence light beams A2 of p-polarization and s-polarization are used and the reflectivities of total reflection light beams are measured and a logarithmic ratio of these reflectivities (two-color ratio of light absorption) is calculated. This ratio is used as a parameter in searching a calibration curve representative of a relation between a pre-tilt angle and a two-color ratio obtained beforehand by another pre-tilt angle measuring method to thereby obtain the pre-tilt angle. Therefore, not the He—Ne laser source 10 but an infrared light source or an ultraviolet light source is used in correspondence with the absorption spectrum of the liquid crystal. The material of the semispherical glass 2 changes with the wavelength of light to be used, for example, silicon, germanium or the like if infrared light is used, and sapphire if ultraviolet light is used.

The optical anisotropy measuring apparatus 30 of Prior Art 4 has advantages of a fine measurement area and the like, which Prior Arts 1 to 3 do not provide. On the other hand, since the semispherical glass 2 is disposed also above the liquid crystal device 22, the position of the measurement area is hard to be visually confirmed from the position above the liquid crystal device 22.

The position of the measurement area may be checked by removing the upper semispherical glass 2 and thereafter the pre-tilt angle is measured by mounting the upper semispherical glass 2. However, this method complicates the measurement work, and in addition there is a possibility that a position displacement may occur while the upper semispherical glass 2 is mounted. If the f-number N is small as in Prior Art 4, the size of the measurement area changes greatly and the measurement precision lowers if the focal point shifts even slightly in an optical axis direction.

The illumination area (measurement area) may be observed through the upper semispherical glass 2 with a microscope objective lens having a long work distance, without dismounting the upper semispherical glass 2. With this method, however, there are restrictions in the size of the semispherical glass 2 and the magnification factor and resolution of a microscope objective lens. In order to eliminate these restrictions, the apparatus may become expensive and the measurement work performance may be degraded.

SUMMARY OF THE INVENTION

It is an object of the present invention to provide an optical characteristic measuring apparatus capable of, e.g., confirming the position of a measurement area with high precision.

It is another object of the present invention to provide an optical characteristic measuring apparatus capable of preventing the works such as the position confirmation from being complicated.

It is still another object of the present invention to provide an optical characteristic measuring apparatus capable of correctly measuring an optical characteristic.

According to one aspect of the present invention, an optical characteristic measuring apparatus is provided having a medium to be inspected, a first light source for applying a light beam to the medium, and an input side optical system for focusing the light beam from the first light source upon a specific interface, the first light source and the input side optical system being disposed so that a portion of the light beam from the first light source is applied to the specific interface at an angle smaller than a critical angle of total internal reflection of the specific interface to measure an optical characteristic of the medium, the optical characteristic measuring apparatus comprising: a first light reception system disposed near the medium for receiving evanescent light generated in the medium when the light beam is applied to the medium, the received evanescent light having a propagation direction bent by the optical heterogeneity of the medium and output along the bent propagation direction different from an original direction of the evanescent light.

The optical characteristic measuring apparatus may further comprise a first photodetector for detecting a light beam transmitted through the first light reception system.

The light beam applied to the medium may be linearly polarized.

The optical characteristic measuring apparatus may further comprise: a second light reception system disposed on an optical path of a light beam totally reflected at the specific interface; a second photodetector for detecting a light beam transmitted through the second light reception system; and filter means disposed between the medium and the second photodetector, the filter means being operating to pass a light beam reflected at the specific interface and not to path a light beam reflected at an interface different from the specific interface.

The light beam applied to the medium may be linearly polarized, and the apparatus may further comprise an analyzer disposed between the medium and the second photodetector.

The filter means may have a light shielding member for shielding the light beam reflected at an interface different from the specific interface.

The light shielding member may be formed with a hole through which the light beam reflected at the specific interface passes.

The optical characteristic measuring apparatus may further comprise medium holding means for holding the medium.

The medium holding means may be made of a semispherical glass member having a flat part and a spherical part and the light beam from the first light source is applied via the medium holding means to the medium.

The first light reception system may be disposed near an area where the light beam from the first light source is reflected at the specific interface, and a position of a measurement area is checked with the first light reception system.

The optical characteristic measuring apparatus may further comprise a first photodetector for detecting a light beam transmitted through the first light reception system.

The optical characteristic measuring apparatus may further comprise a second light source disposed on a side opposite to a side of the first light reception system relative to the medium, wherein a measurement area is illuminated by the second light source.

The first light reception system may be a microscope.

The optical characteristic measuring apparatus may further comprises a variable aperture disposed between the input side optical system and the medium, the variable aperture adjusting a size of a measurement area.

The medium may be a liquid crystal and the apparatus measures the optical anisotropy of the liquid crystal.

The optical characteristic measuring apparatus may further comprise a transparent substrate facing the flat part of the medium holding means, and the liquid crystal is squeezed between the transparent substrate and the flat part.

The liquid crystal may be squeezed between a pair of transparent substrates to constitute a liquid crystal device, the liquid crystal device is held by the medium holding means, refractive index matching liquid is filled in between the liquid crystal device and the medium holding means, and the refractive indices of the liquid crystal device, the medium holding means, and the refractive index matching liquid are set generally equal.

The liquid crystal device may be moved relative to the medium holding means.

Optical anisotropy of the liquid crystal may be detected while the liquid crystal is driven.

DETAILED DESCRIPTION OF THE PREFERRED EMBODIMENTS

Figure 1:
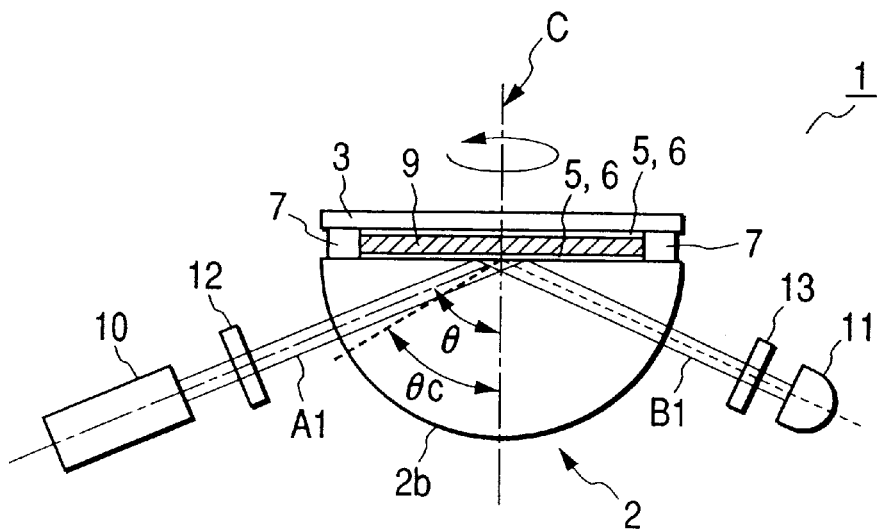
FIG. 1 is a schematic diagram showing an example of the structure of an optical anisotropy measuring apparatus utilizing the TIR method and illustrating an optical anisotropy measuring method.
Figure 2:
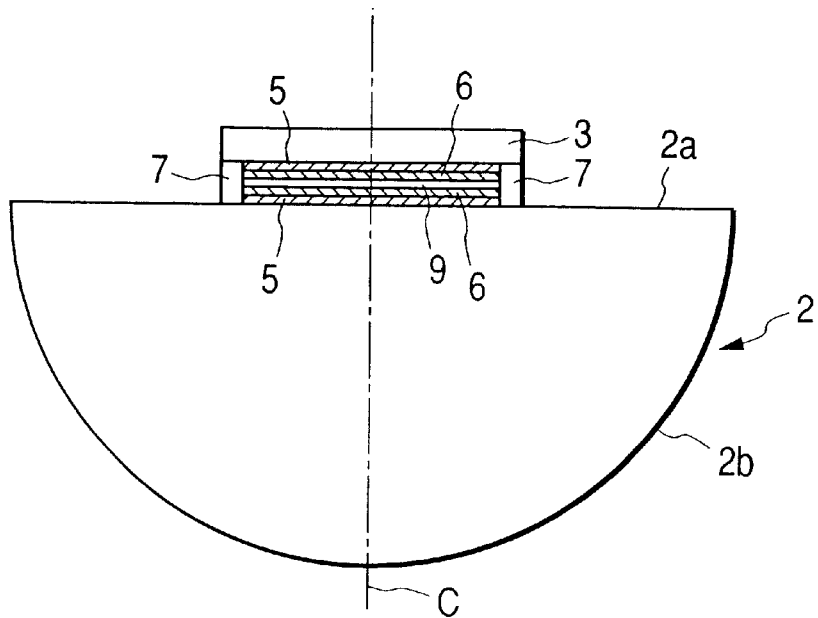
FIG. 2 is a schematic diagram showing the detailed structure of the optical anisotropy measuring apparatus utilizing the TIR method shown in FIG. 1.

Embodiments of the invention will be described with reference to FIGS. 7 to 10. Similar elements to those shown in FIGS. 1 to 6 are represented by using identical reference numerals in FIGS. 7 to 10.

Figure 7:
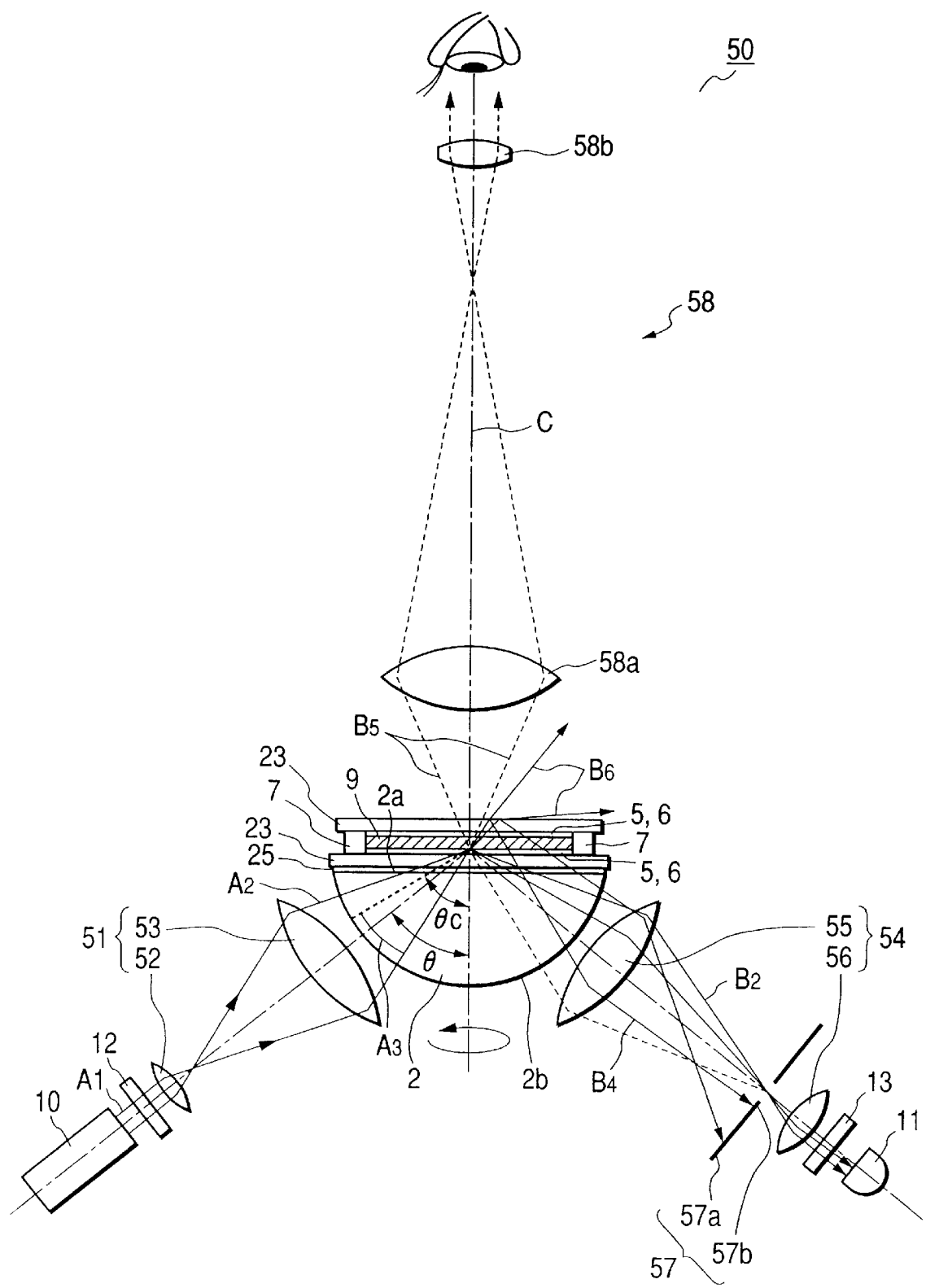
FIG. 7 is a schematic diagram showing an example of the structure of an optical characteristic measuring apparatus according to a first embodiment of the invention.

An optical characteristic measuring apparatus 50 according to an embodiment has, as shown in FIG. 7, a medium 9 whose optical characteristic is measured, and a first light source 10 for applying a light beam A1 to the medium 9. The optical characteristic measuring apparatus 50 has also a polarizer 12 for linearly polarizing the light beam A1 from the first light source 10 and an input-side optical system 51 for converging the light beam A1. An angle between the optical axis of the input side optical system 51 and a normal to a specific interface (lower interface of the medium 9) is represented by θ. An analyzer 13 is disposed on an optical path of a light beam B2 totally reflected at the specific interface of the medium. A second photodetector 11 is disposed near the analyzer 13 and receives the light beam B2 transmitted through the analyzer 13.

The first light source 10 may be any type of a light source so long as it can output light capable of being converged. For example, a laser source (e.g., an He—Ne laser source, an Ar laser source, a semiconductor laser source) or light sources other than a laser source may be used. The input side optical system 51 may be constituted of a lens 52 for diverging the parallel light beam A1 from the first light source 10 and a lens 53 for converging the diverged light beam.

An output side optical system 54 may be disposed between the medium 9 and second photodetector 11 to transform a light beam B2 (hereinafter called a "reflection light beam B2") totally reflected at the specific interface into a parallel light beam. In this case, the output side optical system 54 may be constituted of a lens 55 for converging the reflection light beam B1 and a lens 56 for transforming the converted light beam into a parallel light beam.

The first light source 10 and input side optical system 51 are disposed so that a partial light beam A3 of the incidence light beam is applied to the medium 9 at an angle smaller than the critical angle θc of the specific interface. Therefore, the light beam A3 transmits through the medium 9 and reaches an interface between an upper glass substrate 23 and the air. The total reflection angle at this interface is 33.7° if the reflective index of the glass substrate is 1.8. A partial light beam of the light beam A3 is therefore totally reflected at this interface. As a result, a portion of the light flux A3 is reflected at this interface toward the medium 9, and the remaining portion of the light flux A3 becomes a transmission light flux B6.

A filter means 57 is disposed between the medium 9 and second photodetector 11 so that a light beam B2 totally reflected at the specific interface is passed through the filter means 57 and so that a light beam reflected from an interface different from the specific interface, particularly, a light beam B4 reflected from an interface between the upper glass substrate 23 and air at which a portion of the light beam A3 is reflected, is not transmitted through the filter means 57.

The filter means 57 has a light shielding member 57a (e.g., plate member) disposed on an optical path of the light beam B4 reflected from the interface different from the specific interface, the light shielding member 57a shielding the light beam B4. The light shielding member 57a may be disposed surrounding the optical path of the light beam B2 totally reflected from the specific interface and a hole 57b is formed through the light shielding member 57a in an area corresponding to the optical path of the light beam B2 to allow the light beam B2 to pass through the hole 57b. It is preferable to form this hole 57b at the position where the light beam B2 is focused by the lens 55.

The medium 9 may be held in position by a transparent medium holding means 2. In this case, the medium holding means 2 may be configured in generally a semispherical shape having a flat part 2a and a spherical part 2b so that the incidence light beam A2 is applied via the medium holding means 2 to the medium 9. The material of the medium holding means 2 is preferably a material having a refractive index larger than that of the medium 9. If the medium is a liquid crystal, a material having a refractive index of 1.7 or larger or preferably 1.75 or larger is used (e.g., dense flint glass).

Figure 8:
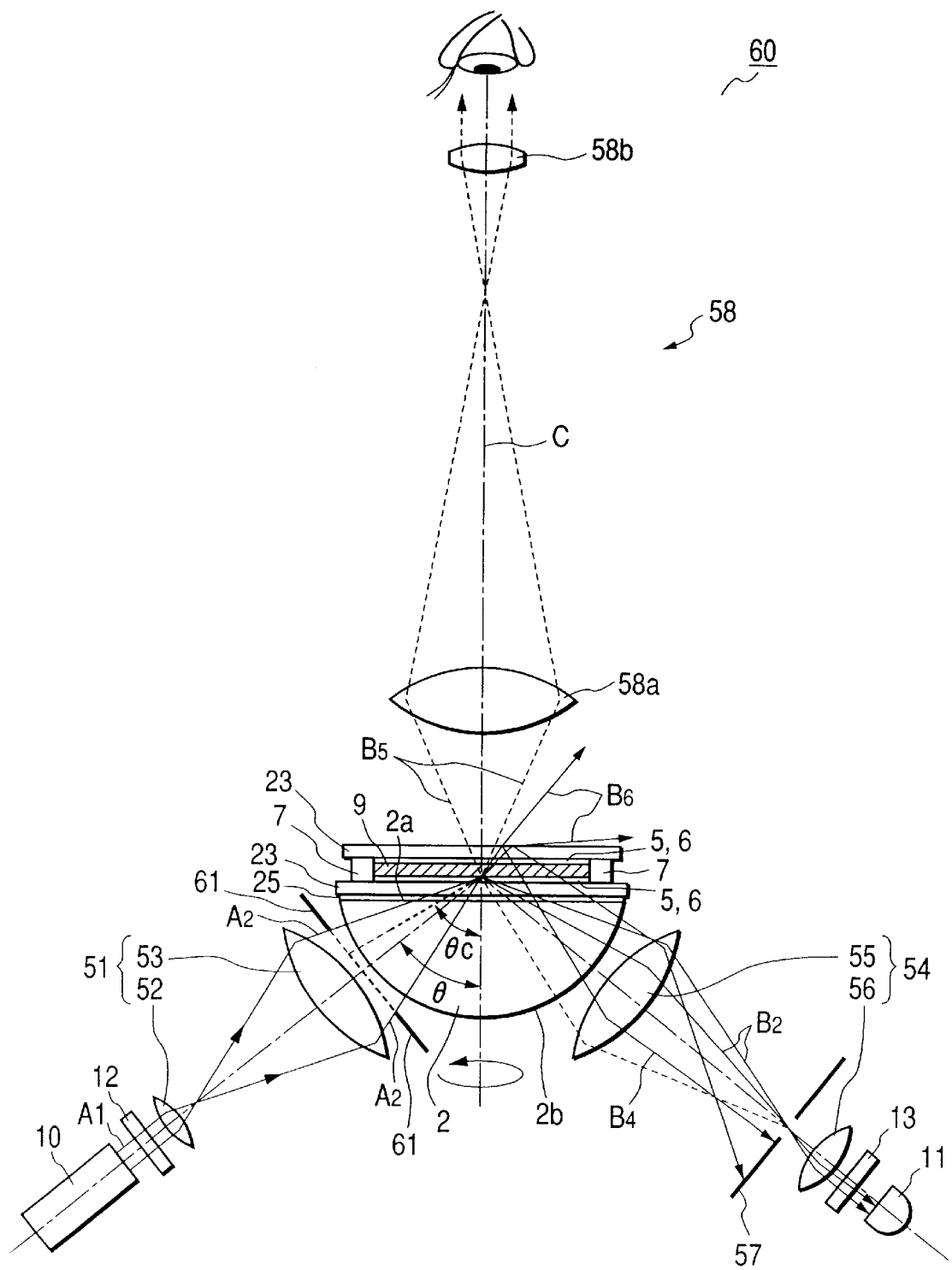
FIG. 8 is a schematic diagram showing an example of the structure of an optical characteristic measuring apparatus according to a second embodiment of the invention.

As shown in FIG. 8, an aperture means 61 capable of stopping down the light beam A2 may be disposed between the input side optical system 51 and medium 9. By stopping down the light beam A2, the measurement area can be made large, and by not stopping down the light beam A2, the measurement area can be made small. In this manner, the size of the measurement area can be adjusted when necessary. As the aperture means 61, a variable aperture may be used. A plurality of fixed apertures having different aperture sizes may be prepared and each fixed aperture is replaced by a desired fixed aperture.

A microscope 58, to be used as a first light reception system, may be disposed above the medium 9 to check the position of the measurement area. Reference symbol 58a in FIG. 8 represents an objective lens and reference symbol 58b represents an eye piece. In order to observe with human eyes, a CCD or the like may be mounted on the microscope to use it as a first photodetector.

The medium 9 may be a liquid crystal to measure the optical anisotropy of the liquid crystal and calculate the pre-tilt angle. The method of holding the liquid crystal may be:

disposing the transparent substrate 23 at the position facing the flat part 2a of the medium holding means and squeezing the liquid crystal 9 between the transparent substrate 23 and flat part 2a; or squeezing the liquid crystal 9 between a pair of transparent substrates 23 to constitute the liquid crystal device 22 and holding the liquid crystal device 22 with the medium holding means 2. In the latter method, the refractive index matching liquid 25 is filled in between the transparent substrate 23 and medium holding means 2, the liquid having generally the same refractive index as that of the transparent substrate 23 and medium holding means 2. In this case, the liquid crystal device 22 may be supported in a freely movable manner by an unrepresented transport mechanism to thereby allow relative motion of the liquid crystal device 2 and medium holding means 2. A micrometer may be mounted on the transport mechanism to measure a motion distance of the liquid crystal device.

The liquid crystal may be driven by applying predetermined signals.

The second photodetector 11 may be an optical power meter, a photomultiplier or the like and has preferably a wide dynamic range.

Next, the optical anisotropy measuring method utilizing the TIR method will be described.

The light beam A1 output from the first light source 10 passes through the polarizer 12 whereat it is linearly polarized, passes through the input side optical system 51 whereat it is converged, and becomes incident upon the medium 9.

A portion (other than A3) of the light beam A2 becomes incident upon the specific interface at an angle larger than the critical angle $\theta c$ and is totally reflected at this specific interface. Evanescent light once enters the medium 9 when the incidence light is totally reflected. Therefore, if the medium has optical anisotropy, after the polarization of the evanescent light is changed, it is reflected and output as the reflection light beam.

Of this reflection light beam B2, only the components having a polarization direction perpendicular to the polarizer 12 are detected with the analyzer 13 and received by the second photodetector 11. In this manner, the optical characteristic such as birefringence of the area near the specific interface of the medium 9 can be measured.

In this case, since the reflection light beam B2 passes through the small hole 57b, it is not shielded by the filter means 57. The light beam B2 reaching the analyzer 13 contains not only the light whose polarization state was changed in the medium 9 but also a small amount of light reflected at the specific interface with its polarization state being unchanged. The light whose polarization state is not changed cannot pass through the analyzer 12 so that it cannot be detected with the second photodetector 11.

Figure 3:
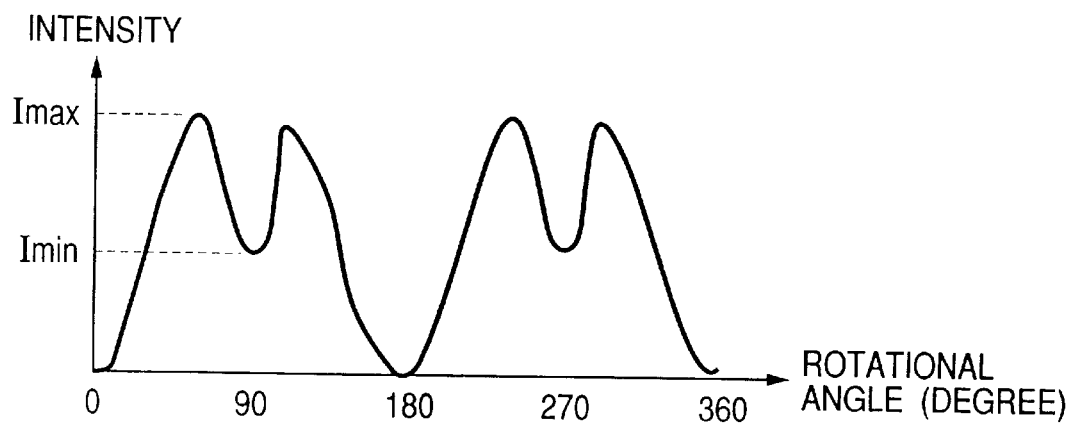
FIG. 3 is a graph showing a characteristic curve representative of the optical anisotropy of liquid crystal.
Figure 4:
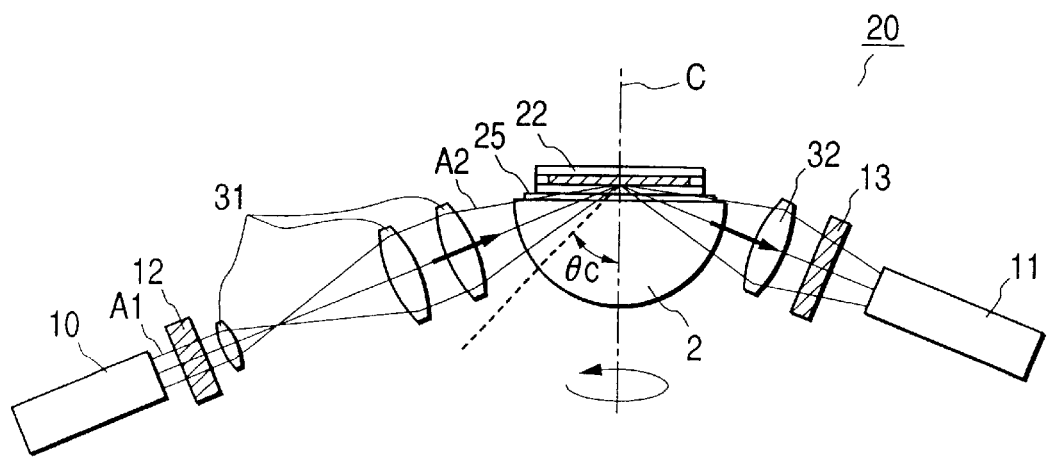
FIG. 4 is a schematic diagram showing another example of the structure of an optical anisotropy measuring apparatus utilizing the TIR method and illustrating an optical anisotropy measuring method.
Figure 5:
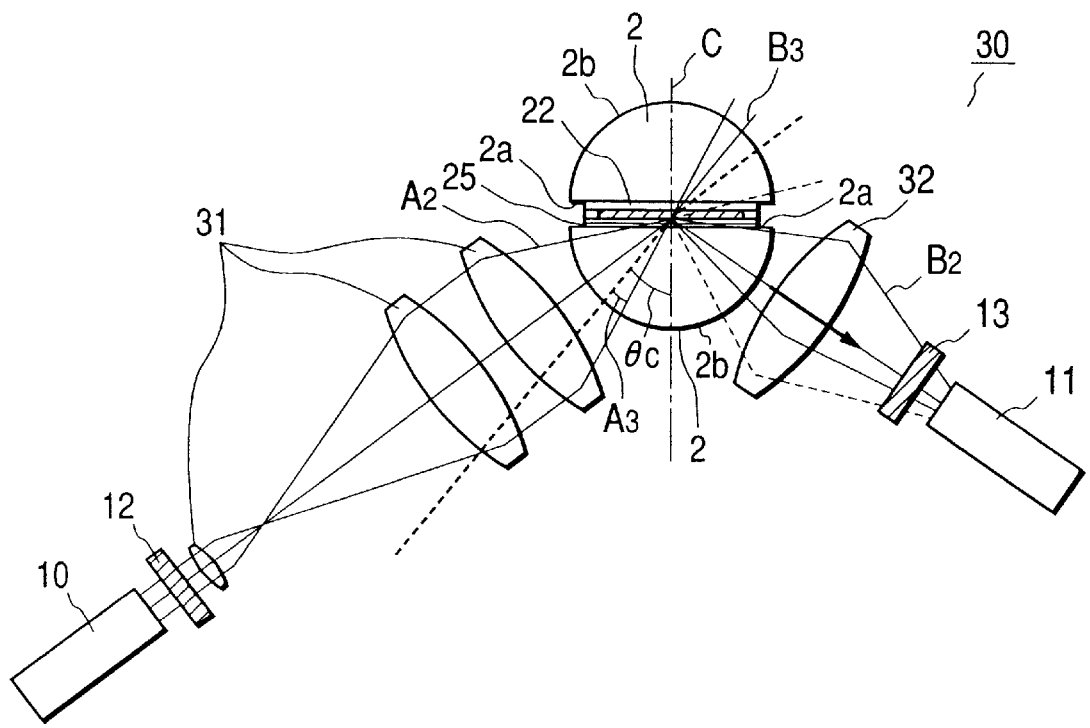
FIG. 5 is a schematic diagram showing another example of the structure of an optical anisotropy measuring apparatus utilizing the TIR method and illustrating an optical anisotropy measuring method.
Figure 6:
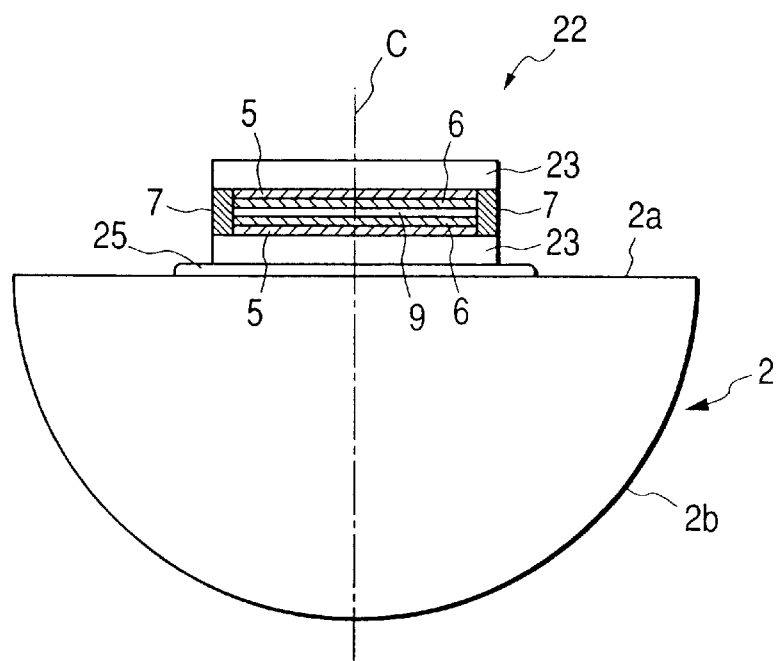
FIG. 6 is a schematic diagram showing the detailed structure of the optical anisotropy measuring apparatus utilizing the TIR method shown in FIG. 5.

By plotting the output (light intensity I) of the photodetector 11 relative to the rotational angle while the medium 9 is rotated about a rotary axis C, a characteristic curve, such as is shown in FIG. 3, can be obtained. If the medium 9 is a liquid crystal, the pre-tilt angle of the liquid crystal can be calculated from a ratio of a light intensity maximum extreme value Imax to a light intensity minimum extreme value Imin (refer to H. P. Hinov et.al., Review Phys. Appl. 15 (1980) 1307–1321 and Jiuzhi Xue et. al., Appl. Phys. Lett. 53 (1988) 2397–2399).

Evanescent light generated in the measurement area is scattered/diffracted by the heterogeneity of the medium 9 if any. Therefore, the propagation direction of the evanescent light is bent and it can be observed from a position above the medium 9. This means that the distribution of heterogeneity of the medium 9 can be observed with a high resolution through illumination by illumination light containing the evanescent light, by using the first light source 10, the input side optical system 51, the first light reception system 58, and unrepresented medium transport mechanism of the apparatus 50. If an illumination light, particularly the light beam B6 transmitted through the medium 9, does not become incident upon the first light reception system 58, measurement under dark field illumination is performed so that the distribution of heterogeneity of the medium 9 can be observed with a high resolution. In other words, a light-scanning-type microscope for scanning the medium 9 under local illumination light containing the evanescent light can be realized by using the components described above. In this case, the light beam transmitted through the light reception system may be detected with a photodetector.

If the medium 9 is liquid crystal, its orientation films 6 have heterogeneity. Therefore, by observing the scattering/refracting light generated by the heterogeneity from the position above the medium 9, the position of the measurement area can be checked. This position check may be performed with human eyes by using a microscope, as the first light reception system 58, or by using a TV camera having a CCD as its photodetector.

Figure 9:
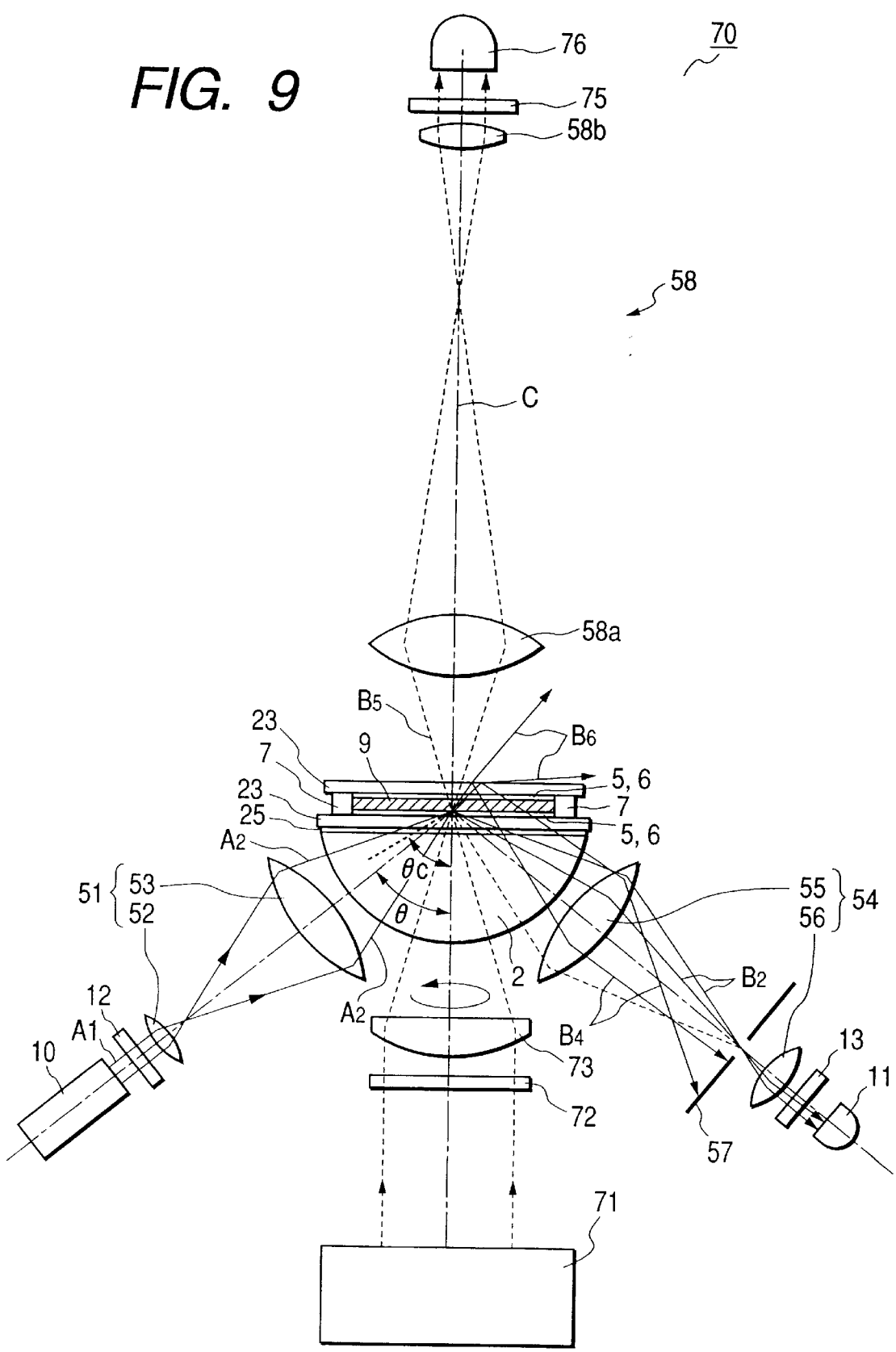
FIG. 9 is a schematic diagram showing an example of the structure of an optical characteristic measuring apparatus according to a third embodiment of the invention.

FIG. 9 shows another example of the structure of an optical characteristic measuring apparatus capable of measuring also a switching characteristic of a liquid crystal device 22. In this optical characteristics measuring apparatus 70, a second light source 71, a polarizer 72, and a lens 73 are disposed under a medium 9 so that a converged light beam can be applied to the measurement area. An analyzer 75 and a first photodetector 76 are disposed above a first light-reception system 58 so that light output from the second light source 71, whose polarization direction was changed by the liquid crystal 9, passes through the analyzer 75 and detected with the first photodetector 76.

Figure 10:
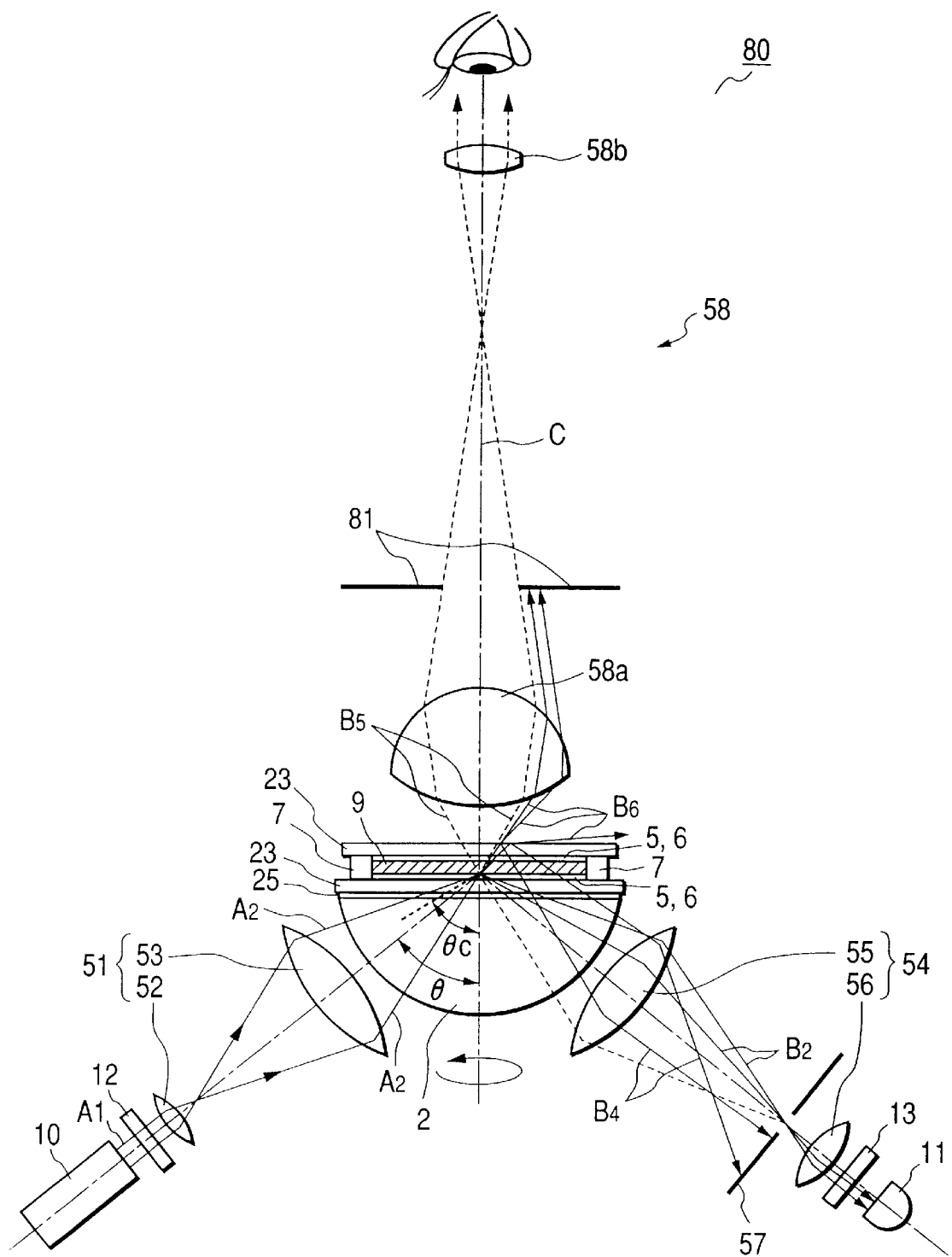
FIG. 10 is a schematic diagram showing an example of the structure of an optical characteristic measuring apparatus according to a fourth embodiment of the invention.

As shown in FIG. 10, the NA of a microscope objective lens 58a may be made large and a variable aperture 81 may be disposed between the objective lens 58a and an eye piece 58b. In this case, it is possible to adjust the field brightness of a microscope 58 and check the position of the measurement area more correctly. The reason for this will be described in the following.

Scattering light B5 and transmission light B6 are radiated upward from the medium 9. However, if the NA of the microscope objective lens 58a is small, light transmitted through the objective lens 58a is only the scattering light B5 as shown in FIG. 7 or the other drawings. In this case, if the measurement area is relatively large and there is a large amount of heterogeneity (e.g., if the medium 9 a liquid crystal, scratches left on the orientation film 6 by the orientation process), which generates the scattering light B5, even if only the scattering light B5 is radiated, the microscope field is sufficiently bright and no practical problem occurs. However, if the measurement area is fine, the probability of presence of such heterogeneity is small so that the field of the microscope 58 becomes dark and the position check becomes difficult.

However, as described above, if the NA of the microscope objective lens 58a is large, not only the scattering light B5 but also the transmission light B6 transmitted through the objective lens 58a as shown in FIG. 10 so that the amount of light in the field of the. microscope 58 becomes large. Since the transmission light B6 can be intercepted by the variable aperture 81, it is possible to adjust the light amount in the field of the microscope 58 so that the position of the measurement area can be correctly checked irrespective of whether the measurement area is large or small.

The variable aperture 81 may not be used, but a large NA of the microscope objective lens 581 is set. Since commercially available, microscope objective lenses have various NA values, an objective lens having an NA capable of properly transmitting the scattering light B5 can be selected and used. However, as already described, if dark field illumination is required in order to check the distribution of heterogeneity of the medium 9, use of the aperture 91 is effective.

In the foregoing, the optical characteristic measuring method using the TIR method has been described. The optical characteristic may be measured by using the calibration curve method. In this case, it is not necessary to use the rotation mechanism for the medium holding means and the analyzer 13. An unrepresented portion for processing data obtained in FIGS. 7 to 10 with a computer is obviously different from that for the TIR method.

Next, the advantageous effects of the embodiment will be described.

According to the embodiment, the partial light beam A3 of the incidence light beam is applied to the medium 9 at an angle smaller than the critical angle θc of the specific interface. Accordingly, the measurement area (light-beam applied region) at the specific interface can be made approximately circular and can be made fine.

Since the first light reception system 58 is disposed above the medium 9, not only can the heterogeneity of the medium 9 can be observed with a high resolution, but also the distribution of the heterogeneity can be observed with a high contrast under the dark-field illumination by properly selecting the NA of the first light reception system.

Further, the filter means 5 is disposed between the medium 9 and second photodetector 11 to pass the light beam B2 totally reflected at the specific interface and not to pass the light beam B4 reflected from the interface different from the specific interface. Accordingly, the second photodetector 11 can receive only the light beam B2 totally reflected from the specific interface so that the measurement of an optical characteristic becomes precise.

Since the filter means 57 is disposed in the above manner, the upper semispherical glass 2 described with Prior Art 2 is not necessary. Therefore, the upper semispherical glass 2 is not necessary to be mounted after the position of the measurement area is checked, so that the position of the measurement area can be checked easily and precisely.

As in Prior Art 4, if the measurement area is to be moved, only the liquid crystal device 22 is required to be moved while the upper and lower semispherical glasses 2 are integrally fixed. Therefore, the structure of the transport mechanism becomes large and complicated. With the above embodiment, however, since the upper semispherical glass is not necessary so that the structure of the transport mechanism becomes simple.

If the liquid crystal device 22 is made movable as described earlier, a variation in distribution of the optical characteristics or the like can be easily detected by changing the measurement area. If the motion distance of the liquid crystal device 22 is measured with a micrometer, it is possible to measure the optical characteristic as a function of the position of the measurement area.

If the measurement area is small, it is necessary to perform a preliminary adjustment with high precision in order to maintain measurement precision. Therefore, if the measurement area is not required to be small, the measurement work becomes cumbersome in correspondence with the amount of the adjustment work to be performed with high precision. In this case, the variable aperture 61 disposed between the input-side optical system 51 and medium 9 can adjust the size of the measurement area and improve the efficiency of the measurement work.

If the apparatus 70 shown in FIG. 9 is used for measuring a pre-tilt angle by driving the liquid crystal, the second photodetector 11 can measure the switching characteristic of the liquid crystal only in an area near the liquid crystal interface and the first photodetector 76 can measure the switching characteristic of the bulk liquid crystal. Through a comparison between these measured results, effective information on developing a liquid crystal device can be obtained. Through comparison between the measured pre-tilt angle and these switching characteristics, orientation techniques and liquid crystal materials can be developed while taking into consideration of the performance of liquid crystal devices.

Next, an embodiment of the invention will be described with reference to FIG. 7.

In this invention, an optical characteristic of the liquid crystal 9 as the medium to be inspected is measured by using visible light (wavelength: 380 to 800 nm) from various laser sources, a mercury lamp or the like.

In order to measure the optical characteristic with visible light, it is essential to fill a space between the interface of the lower semispherical glass 2 and the liquid crystal device 22, which function as the total internal reflection optical system, with the refractive index matching liquid 25 having a refractive index higher than that of the liquid crystal.

The reason for this is as in the following. Evanescent light is generated in the liquid crystal 9 when the incidence light is totally reflected at the specific interface of the liquid crystal device 22. However, if the space between the interface 2a of the lower semispherical glass 2 and the lower surface of the lower semispherical glass substrate 23 is 1 $\mu$m or larger, the light beam A2 is totally reflected at the interface of the lower semispherical glass 2 and does not reach the liquid crystal 9.

If the refractive index matching liquid 25 is not filled in the space and this space is maintained several tenths of the wavelength of visible light, it is impossible to maintain the lower semispherical glass 2 and liquid crystal device 22 movable.

The medium to be used by the invention includes those materials having optical anisotropy such as bio tissues like cells, diffraction grating, material having birefringence distribution, liquid crystals, and crystals.

(First Embodiment)

In the first embodiment, as shown in FIG. 7, a semispherical glass member (hereinafter called a "semispherical glass 2") was used as the medium holding means 2. The liquid crystal device 22 was mounted on the flat part 2a of the semispherical glass 2. This liquid crystal device 22 was formed by forming the transparent electrodes 5 and orientation films 6 on the surfaces of a pair of glass substrates 23 and by squeezing the liquid crystal (medium to be inspected) 9 between the glass substrates 23. The refractive index matching liquid 25 was filled in between the liquid crystal device 22 and semispherical glass 2.

As the first light source 10, an He—Ne laser source was used, and the output side optical system 54 was disposed between the semispherical glass 2 and second photodetector 11. The filter means 57, constituted of the light shielding member 57a and hole 57b, was disposed between the lenses 55 and 56 of the output side optical system 54.

The microscope 58 was disposed above the liquid crystal device 22 to observe the position of the measurement area.

The pre-tilt angle of the liquid crystal device 22 was calculated by using the apparatus 50. Similar advantageous effects to those of the embodiment described earlier were obtained.

(Second Embodiment)

In this embodiment, as shown in FIG. 8, the variable aperture (aperture means) 61 was disposed between the input side optical system 51 and semispherical glass 2 to stop down the incidence light beam A2. The other structures were similar to the first embodiment.

Also in this embodiment, similar advantageous effects to those of the embodiment described earlier were obtained.

(Third Embodiment)

In this embodiment, as shown in FIG. 9, the second light source 71, the polarizer 72, and the lens 73 were disposed under the semispherical glass 2 to focus the converged light beam upon the measurement area. The analyzer 75 and first photodetector 76 were disposed above the first light reception system 58 to detect light in real time with the first photodetector 76, the light being radiated from the second light source 71 and the polarization direction of the light being changed by the liquid crystal device 22 under operation, and at the same time to detect light in real time with the second photodetector 11, the light being radiated from the first light source and totally reflected at the specific interface of the liquid crystal 9. The other structures were similar to the first embodiment.

With this embodiment, it was possible to compare and study the pre-tilt angle and switching characteristic of the liquid crystal in an area near the specific interface and the switching characteristic of the bulk liquid crystal.

(Fourth Embodiment)

In the fourth embodiment, as shown in FIG. 10, the NA of the microscope objective lens 58a was made large, and the variable aperture 81 was disposed between the objective lens 58a and eye piece 58b. The other structures were similar to the first embodiment.

With this embodiment, it was possible to adjust the brightness of the field of the microscope 58 and check the position of the measurement area more correctly.

As described so far, according to the present invention, since the measurement area (illumination area) of the medium is made small, the heterogeneity distribution of the medium can be observed with a high resolution through the first light reception optical system disposed above the medium, and at the same time, by adjusting the NA of the first light reception optical system, observation under substantially dark field illumination at a high contrast becomes possible.

Further, according to the present invention, the filter means is disposed between the medium and second photodetector to pass the light beam reflected at the specific interface and not to pass the light reflected at the interface different from the specific interface. Accordingly, the second photodetector receives only the light beam totally reflected at the specific interface so that the optical characteristic can be measured correctly.

Since the filter means is disposed as described above, the upper semispherical glass as in Prior Art 4 is not necessary. Accordingly, it is not necessary to mount the upper spherical glass after the position of the measurement area is checked, so that the position of the measurement area can be checked easily and precisely.

Since the upper semispherical glass as in Prior Art 4 is not necessary, the structure of the transport mechanism for moving the measurement area can be made simple.

If the variable aperture is disposed between the input side optical system and medium and the size of the measurement area is adjusted by the variable aperture, it is not necessary to perform an adjustment, work such as a check of the position of the measurement area at unnecessarily high precision, so that the efficiency of the measurement work can be improved.

What is claimed is:

1. An optical characteristic measuring apparatus, for measuring an optical characteristic of a medium to be inspected, having a light source for applying a light beam to the medium and an input side optical system for focusing the light beam from the light source upon a specific interface of the medium, the light source and the input side optical system being disposed so that a portion of the light beam from the light source is applied to the specific interface at an angle less than a critical angle of total internal reflection at the specific interface and so that a portion of the light beam from the light source is applied to the specific interface at an angle greater than the critical angle of total internal reflection at the specific interface to produce evanescent light in the medium to measure an optical characteristic of the medium, said optical characteristic measuring apparatus comprising:

an evanescent light beam light reception system disposed near the medium for receiving a light beam emitted in a direction different from an original propagation direction of the evanescent light produced in the medium when the light beam from the light source is applied to the medium, the received light beam being generated because of a portion of the evanescent light being deflected by optical heterogeneity of the medium.

2. An optical characteristic measuring apparatus according to claim 1, further comprising a photodetector for detecting a light beam transmitted through said evanescent light beam light reception system.

3. An optical characteristic measuring apparatus according to claim 1 or 2, wherein the light source applies a linearly polarized light beam to the medium.

4. An optical characteristic measuring apparatus according to claim 1, further comprising:

a totally reflected light beam light reception system disposed on an optical path of a light beam totally reflected at the specific interface of the medium for receiving the totally reflected light beam;

a photodetector for detecting a light beam transmitted through said totally reflected light beam light reception system; and filter means disposed between the medium and said photodetector, said filter means passing a light beam reflected at the specific interface of the medium and not passing light beams reflected at interfaces of the medium different from the specific interface.

5. An optical characteristic measuring apparatus according to claim 4, further comprising an analyzer disposed between the medium and said photodetector, wherein the light source applies a linearly polarized light beam to the medium.

6. An optical characteristic measuring apparatus according to claim 4, further comprising a variable aperture, disposed between the input side optical system and the medium, for adjusting a size of a measurement area of the medium.

7. An optical characteristic measuring apparatus according to claim 4, wherein said filter means comprises a light shielding member for shielding light beams reflected at the interfaces different from the specific interface.

8. An optical characteristic measuring apparatus according to claim 7, wherein said light shielding member has a hole through which the light beam reflected at the specific interface passes.

9. An optical characteristic measuring apparatus according to claim 4, further comprising medium holding means for holding the medium.

10. An optical characteristic measuring apparatus according to claim 9, wherein said medium holding means comprises a semispherical glass member having a flat portion and a spherical portion and the light source applies the light beam to the medium through said medium holding means.

11. An optical characteristic measuring apparatus according to claim 4, wherein said evanescent light beam light reception system (i) is disposed near a measurement area of the medium where the light beam from the light source is reflected at the specific interface, and (ii) is used to check a position of the measurement area.

12. An optical characteristic measuring apparatus according to claim 11, further comprising a photodetector for detecting a light beam transmitted through said evanescent light beam light reception system.

13. An optical characteristic measuring apparatus according to claim 12, further comprising a light source, disposed on a side of the medium opposite to a side of said evanescent light beam light reception system, for illuminating a measurement area of the medium.

14. An optical characteristic measuring apparatus according to claim 11, wherein said evanescent light beam light reception system is a microscope.

15. An optical characteristic measuring apparatus according to any one of claims 4 to 14, wherein the medium is a liquid crystal and said apparatus measures optical anisotropy of the liquid crystal.

16. An optical characteristic measuring apparatus according to claim 9, further comprising a transparent substrate facing the flat portion of said medium holding means, wherein the liquid crystal is located between said transparent substrate and the flat portion of said medium holding means.

17. An optical characteristic measuring apparatus according to claim 15, further comprising a pair of transparent substrates between which the liquid crystal is located to constitute a liquid crystal device, wherein said medium holding means holds said liquid crystal device, refractive index matching liquid is filled in between said liquid crystal device and said medium holding means, and the refractive indices of said liquid crystal device, said medium holding means, and the refractive index matching liquid are set to be nearly equal.

18. An optical characteristic measuring apparatus according to claim 17, further comprising a transport mechanism for moving said liquid crystal device relative to said medium holding means.

19. An optical characteristic measuring apparatus according to claim 18, wherein said apparatus measures optical anisotropy of the liquid crystal while the liquid crystal is moved by said transport mechanism.

* * * * *

UNITED STATES PATENT AND TRADEMARK OFFICE
CERTIFICATE OF CORRECTION

PATENT NO. : 6,215,549 B1
DATED : April 10, 2001
INVENTOR(S) : Takashi Suzuki et al.

It is certified that error appears in the above-identified patent and that said Letters Patent is hereby corrected as shown below:

Column 2,
Line 6, "once the liquid crystal" should read -- the liquid crystal once --.

Column 3,
Line 31, "substrate" should read -- substrates --.

Column 4,
Line 27, "Oc" should read -- θc --.

Column 6,
Line 34, "comprises" should read -- comprise --.

Column 10,
Line 3, "and" should read -- and an --.
Line 60, "the." should read -- the --.

Column 11,
Line 1, "available," should read -- available --.
Line 25, "can be" should read -- can --.

Column 12,
Line 12, "of the" should read -- the --.

Signed and Sealed this

Second Day of April, 2002

Attest:

*Attesting Officer*

JAMES E. ROGAN
*Director of the United States Patent and Trademark Office*